US006245351B1

(12) United States Patent
Nara et al.

(10) Patent No.: US 6,245,351 B1
(45) Date of Patent: *Jun. 12, 2001

(54) CONTROLLED-RELEASE COMPOSITION

(75) Inventors: Eiji Nara, Mishima-gun; Yohko Akiyama, Ohmihachiman; Kenji Nakamura, Izumi, all of (JP)

(73) Assignee: Takeda Chemical Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/812,939

(22) Filed: Mar. 4, 1997

(30) Foreign Application Priority Data

Mar. 7, 1996 (JP) ........................................ 8-50613

(51) Int. Cl.$^7$ ................................................ A61K 9/62

(52) U.S. Cl. .................. 424/461; 424/462; 424/495; 424/497; 424/480; 523/122; 514/282

(58) Field of Search ................. 523/122; 428/402.22, 428/402.24, 422, 438, 426; 424/461, 462, 495, 497, 480, 482; 524/40, 41, 42, 43, 46, 556

(56) References Cited

U.S. PATENT DOCUMENTS

| | | | |
|---|---|---|---|
| 3,362,881 | * | 1/1968 | Eberharot et al. .................. 424/482 |
| 4,083,949 | | 4/1978 | Benedikt ............................... 424/19 |
| 4,612,250 | * | 9/1986 | Takeda et al. ....................... 428/500 |
| 5,047,244 | * | 9/1991 | Sanvordeker et al. .............. 424/435 |
| 5,112,621 | | 5/1992 | Stevens et al. ..................... 424/497 |
| 5,593,694 | * | 1/1997 | Hayashida et al. ................. 424/468 |
| 5,639,476 | * | 6/1997 | Oshlack et al. ...................... 424/40 |
| 5,801,220 | * | 9/1998 | Desai et al. ......................... 524/13 |
| 5,882,682 | * | 3/1999 | Rork et al. ......................... 424/473 |

FOREIGN PATENT DOCUMENTS

| | | |
|---|---|---|
| 342 203 | 7/1977 | (AT) . |
| 2068366 | 11/1992 | (CA) . |
| 0 052 076 A1 | 5/1982 | (EP) . |
| 0 210 540 A1 | 2/1987 | (EP) . |
| 0 284 407 A2 | 9/1988 | (EP) . |
| 0 284 408 A1 | 9/1988 | (EP) . |
| 0 305 918 A1 | 3/1989 | (EP) . |
| 0 320 097 | 6/1989 | (EP) . |
| 0 322 277 | 6/1989 | (EP) . |
| 355 560 | 10/1989 | (EP) . |
| 0 347 024 | 12/1989 | (EP) . |
| 0 377 518 A1 | 7/1990 | (EP) . |
| 0 453 001 A1 | 10/1991 | (EP) . |

(List continued on next page.)

OTHER PUBLICATIONS

Posch et al. EP682945—Nov. 1995 Oral Sustained Release Prep.*
Conte, et al. EP 635265—Jan. 1995 Controlled Release Pharmaceutical.*
Derwent Abstract 88–266524/38 of JP 0774166–B 1988.
Derwent Abstract 95–290323/38 of JP 07188057–A, 1995.
Derwent abstract of EP–A–052076 (WPI Accession No. 82–39785E/198220).

*Primary Examiner*—Neil S. Levy
(74) *Attorney, Agent, or Firm*—Wenderoth, Lind & Ponack, L.L.P.

(57) ABSTRACT

A controlled-release composition comprising a drug-containing core coated with a coating composition containing a water-insoluble substance and a swellable polymer having no basic groups which is capable of maintaining an almost constant drug concentration in plasma over an extended period of time to ensure sustained drug action in the body.

22 Claims, 3 Drawing Sheets

-○- CHANGES OVER TIME IN THE AMOUNT OF DRUG RELEASED (pH 1.2)

-●- CHANGES OVER TIME IN THE AMOUNT OF DRUG RELEASED (pH 6.8)

FOREIGN PATENT DOCUMENTS

| | | |
|---|---|---|
| 0 484 186 A1 | 5/1992 | (EP) . |
| 0 548 448 A1 | 6/1993 | (EP) . |
| 0 630 646 A1 | 12/1994 | (EP) . |
| 0 631 781 A1 | 1/1995 | (EP) . |
| 0 647 448 A1 | 4/1995 | (EP) . |
| 0 807 433 | 11/1997 | (EP) . |
| 905000 * | 9/1962 | (GB) .................................. 424/482 |
| 6-247844 | 2/1993 | (JP) . |
| 88/03795 | 6/1988 | (WO) . |
| 94/22431 | 10/1994 | (WO) . |
| 95/14460 | 6/1995 | (WO) . |

* cited by examiner

−◦− CHANGES OVER TIME IN DRUG RELEASED (pH 1.2)
−•− CHANGES OVER TIME IN DRUG RELEASED (pH 6.8)

CONTROLLED-RELEASE COMPOSITION

BACKGROUND OF THE INVENTION

1. Field of the Invention

The present invention relates to a controlled-release composition comprising a drug-containing core coated with a coating composition comprising a water-insoluble substance and a swellable polymer having no basic groups.

2. Description of the Related Art

Controlled-release preparations of drugs, especially sustained-release preparations, are advantageous in that administration frequency can be reduced by maintaining a constant plasma concentration of drug over an extended period of time to ensure sustained effect of the active ingredient. In addition, such preparations are also expected to decrease side effects by suppressing the rapid rise in the blood level of drug. Therefore, a large number of controlled-release systems, including capsular preparations comprising a drug-containing core coated with a release-controlling film (Japanese Patent Unexamined Publication Nos. 145056/1995 and 206679/1995, Canadian Patent Unexamined Publication No. 2,068,366, WO 94/22431, EP0377518, EP0630646, EP0631781, Japanese Patent Examined Publication No. 72130/1995). In such capsular preparation, the release-controlling film is made of the hydrophobic polymer containing a hydrophilic or a water-soluble substance, and release or releasing rate of the drug is designed to control by the formula of the film.

There are many drugs whose absorption rate in the large intestine is not as good as in the small intestine. In view of the fact that controlled-release compositions in the form of oral preparations pass through the small intestine in relatively short time, for example, active ingredient generally reaches the large intestine in about 5–6 hours in such composition, it is difficult to design a sustained-release preparation of such drugs for once- or twice-a-day administration that is required to maintain an effective plasma concentration of drug for 12–24 hours, because the absorption of the drugs would be suppressed after 5–6 hours following administration. Also, even a drug absorbable from the entire gastrointestinal tract often undergoes extremely suppressed drug release in the large intestine due to drug concentration reduction in the release-controlling preparation and water loss in the lower gastrointestinal tract during passage through the gastrointestinal tract. Thus it is difficult to obtain a satisfactory sustained-release preparation, especially those of the drugs mainly absorbed at small intestine.

SUMMARY OF THE INVENTION

With this situation in mind, the present inventors made extensive investigation to develop a controlled-release composition for oral administration coated with a coating composition which is capable of releasing the drug at higher rates in the intestinal tract than in the stomach to maintain an almost constant plasma concentration of drug and ensure effect of drug in the body for an extended period of time. Based on the findings that a controlled-release composition comprising a drug-containing core coated with a coating composition comprising a water-insoluble substance and a swellable polymer having no basic groups shows greater release rates in the small and large intestines than in the stomach through which it passes just after oral administration the present invention is developed.

Accordingly, the present invention relates to;

(1) a controlled-release composition comprising a drug-containing core coated with a coating composition comprising a water-insoluble substance and a swellable polymer having no basic group, (2) the controlled-release composition of (1), wherein said water-insoluble substance has film-forming ability, (3) the controlled-release composition of (1), wherein said water-insoluble substance is a cellulose ether or cellulose ester, (4) the controlled-release composition of (1), wherein said water-insoluble substance is ethyl cellulose.

(5) the controlled-release composition of (1), wherein said swellable polymer has an acidic dissociating group and shows pH-dependent swelling.

(6) the controlled-release composition of (1), wherein said swellable polymer is a crosslinked acrylic polymer.

(7) the controlled-release composition of (5), wherein the molecular weight of said swellable polymer is about 1,000,000 to about 10,000,000.

(8) the controlled-release composition of (1), wherein the viscosity of said swellable polymer is about 1,500 to about 60,000 cp in 0.2% neutral solution.

(9) the controlled-release composition of (1), wherein said coating composition may further contain a hydrophilic substance.

(10) the controlled-release composition of (9), wherein said hydrophilic substance is a polysaccharide having a hydroxyalkyl group or carboxyalkyl group.

(11) the controlled-release composition of (9), wherein said hydrophilic substance is hydroxypropylmethyl cellulose.

(12) the controlled-release composition of (1), wherein the ratio of said coating composition to said core is not lower than 1% (w/w).

(13) the controlled-release composition of (1), wherein the content ratios of the water-insoluble substance and swellable polymer in said coating composition are about 40 to about 95% (w/w) and about 1 to about 40% (w/w), respectively.

(14) the controlled-release composition of (9), wherein the content ratios of the water-insoluble substance, swellable polymer and hydrophilic substance in said coating composition are about 40 to about 95% (w/w), about 1 to about 40% (w/w) and 0 to about 40% (w/w), respectively.

(15) the controlled-release composition of (1), wherein said water-insoluble substance is ethyl cellulose and said swellable polymer is a crosslinked acrylic polymer.

(16) the controlled-release composition of (1), wherein said drug is an opioid compound.

(17) the controlled-release composition of (14), wherein said drug is morphine or a salt thereof.

(18) the controlled-release composition of (1), wherein said drug is a sympathamimetics.

(19) the controlled-release composition of (1), wherein the content of said drug is not lower than 0.5% (w/w).

(20) the controlled-release composition of (1) in the form of granules, fine granules, tablets or capsules.

(21) a coating composition comprising a water-insoluble substance and a swellable polymer having no basic groups.

(22) the coating composition of (21), which further contains a hydrophilic substance.

(23) A method of producing a controlled-release composition which comprises coating a drug-containing core with a coating composition comprising a water-insoluble substance and a swellable polymer having no basic group.

(24) use of a coating composition comprising a water-insoluble substance and a swellable polymer having no basic group for manufacturing a medicament for a once daily oral treatment of a drug.

(25) a method for the treatment of pain-associated condition which comprises administering to a mammal in need thereof an effective amount of medicament containing the controlled-release composition of (17) or (18).

In the Figures., —○— indicates the changes over time in the amount of drug (morphine hydrochloride) released at pH 1.2; —●— indicates the changes over time in the amount of drug (morphine) released at pH 6.8.

Figure 3:
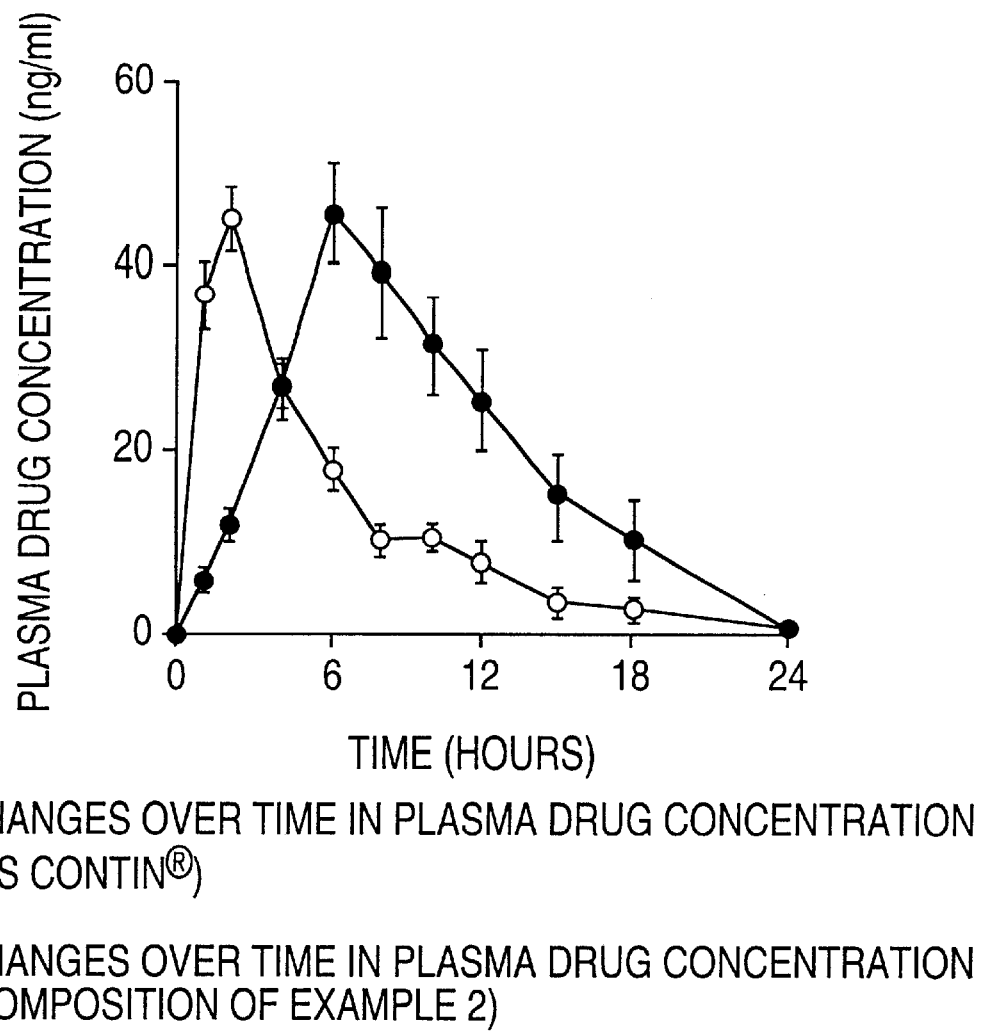

FIG. 3 shows the changes over time in plasma drug (morphine) concentration after administration to fasted beagle dogs.

In the Figure, —●— indicates the changes over time in plasma concentration of drug (morphine) after administration of the composition obtained in Example 9; —○— indicates the changes over time in plasma concentration of drug (morphine hydrochloride) after administration of the control MS Contin®.

DETAILED DESCRIPTION OF THE INVENTION

Examples of the drug for the present invention include, but are not limited to, opioid compounds such as morphine or pharmacologically acceptable salts thereof (e.g., hydrochloride, sulfate), hydromorphone, oxycodone, methadone, meperidine, dihydrocodeine, codeine, dihydromorphine, buprenorphine and fentanyl; antiinflammatory agents such as Naploxen Na, isopropylantipyrine HCl, ibuprofen, ketoprofen, diclofenac Na; sympathomimetics such as ephedrine HCl, salbutamol sulfate, terbutaline sulfate and phenylpropanolamine HCl; anti-allergic drugs such as phenylamine and terfenadine; antihystamines such as chlorpheniramine maleate, diphenhydramine HCl and clemastine fumarate; cardiac drugs such as procainamide hydrochloride, propranolol hydrochloride and quinidine sulfate; antihypertensive drugs such as metoprolol, captopril, hydralazin HCl and diltiazem HCl; antibiotics such as Penicillin V Potassium, Cloxacillin Na, Metronidazole hydrochloride, amoxicillin, cephalexin and clarithromycin; bronchodilators such as theophylline and salbutamol; anti-arrhythmic drugs such as procainamide and quinidine; antineoplastics such as flutamide and fluorouracil; anticonvulsants such as phenytoine Na, ethosuximide and valproate Na; central nervous-acting substances such as chlopromazine hydrochloride, diazepam and perphenazine; gastrointestinal agents such as ranitidine HCl, cimetidine famotidine, omeprazole and lansoprazole; antidiabetic agents such as acarbose voglibose and tolbutamide; cholinergir agent such as bethanecol chloride, neostigumine bromide and carbachol; vitamins; amino acids; and peptides.

Basic drugs are preferably used, among others.

Of these drugs, opioid compounds are preferably used, with greater preference given to morphine or pharmacologically acceptable salts thereof. Such the salt includes an inorganic acid salt such as hydrochloride, sulfate and phosphate, and an organic acid salt such as tartrate and bitartrate. In case of morphine, hydrochloride and sulfate are generally used as pharmacologically acceptable salt.

The water-insoluble substance for the present invention is not subject to limitation, as long as it is capable of forming a film. Specifically, useful water-insoluble substances include cellulose ethers such as ethyl cellulose and butyl cellulose: cellulose esters such as cellulose acetate and cellulose propionate; polyvinyl esters such as polyvinyl acetate and polyvinyl butyrate; acrylic polymers such as acrylic acid and methacrylic acid copolymers, methyl methacrylate copolymers, ethoxyethyl methacrylates, cynaoethyl methacrylate, aminoalkyl methacrylate copolymer, poly (acrylic acid), poly (methacrylic acid), methacrylic acid alkylamide copolymer, poly (methyl methacrylate), polymethacrylate, polyacrylamide, aminoalkyl methacrylate copolymer, poly (methacrylic acid anhydride), and glycidyl methacrylate copolymers, more specifically EodragitTM copolymers (Rohm & Pharma): Eudragit RS (ethyl acrylate/methyl methacrylate/chlorotrimethylammonium methacrylate polymer: 100L, PML, 30DL, 100, PM and 30D); hydrogenated oils such as hydrogenated castor oil (e.g. Lubri wax); waxes such as carnauba wax; monoglycerides; triglycerides paraffin; and polyglycerol fatty acid esters.

Of these water-insoluble substances, cellulose esters are preferably used, with greater preference given to ethyl cellulose. When a cellulose ester is used as the water-insoluble substance, its viscosity is normally about 5 to about 120 centipoise (cp) in 5% solution, preferably about 5 to about 50 cp.

The swellable polymer for the present invention, which has no basic groups, is exemplified by polymers showing little pH dependency in swelling and polymers having an acidic dissociating group and showing pH-dependent swelling.

Of these swellable polymers, those having an acidic dissociating group such that little swelling occurs at acidic pH levels as in the stomach and increased swelling occurs at neutral pH levels as in the small and large intestines is preferably used.

Examples of the polymers shows little pH dependency in swelling include hydroxypropyl celluloses, such as high-viscosity hydroxypropyl cellulose (viscosity about 1,000 to about 4,000 cp in 2% aqueous solution at 200° C.) and low-substitutional hydroxypropyl cellulose; etc.

Examples of the polymers having an acidic dissociating group, and showing pH-dependent swelling include crosslinked acrylic polymers, such as Carbomer™ 934P, 940, 941, 974P, 980 and 1342, polycarbophil, calcium polycarbophil (all produced by BF Goodrich Company), and HIVISWAKO™ 103, 104, 105 and 304 (all produced by Wako Pure Chemical). The viscosity of such pH-dependent swelling polymer is about 1,500 to about 60,000 cp in 0.2% neutral solution, preferably about 3,000 to about 50,000 cp. Molecular weight is about 1,000,000 to about 10,000,000, preferably about about 1,000,000 to about 5,000,000, and more preferably about 1,000,000 to about 3,500,000.

In the controlled-release composition of the present invention (hereinafter briefly referred to as the composition of the present invention), the coating composition may further contain a hydrophilic substance.

In such case, the hydrophilic substances include polysaccharides that may have a sulfate group, such as pullulan, dextrin and alkali metal salt of alginic acid; polysaccharides having a hydroxyalkyl group or carboxyalkyl group, such as hydroxypropyl cellulose, hydroxypropylmethyl cellulose and carboxymethyl cellulose sodium; methyl cellulose; polyvinylpyrrolidone; polyvinyl alcohol; and polyethylene glycol.

Of these hydrophilic substances, polysaccharides having a hydroxyalkyl group or carboxyalkyl group are preferably used, with greater preference given to hydroxypropylmethyl cellulose.

The content ratio of water-insoluble substance in the coating composition of the present invention is about 40 to about 95% (w/w), preferably about 60 to about 90% (w/w); the content ratio of swellable polymer is about 1 to about 40% (w/w), preferably about 5 to about 40% (w/w). The coating composition may further comprise a hydrophilic substance. In such case, the content ratio of hydrophilic substance in the coating composition is 0 to about 40% (w/w), preferably 0 to about 30% (w/w), especially about 1to about 30% (w/w).

The composition of the present invention is produced by preparing a drug-containing core, and coating the resulting core with a liquid coating composition comprising a water-insoluble substance and a swellable polymer either thermally dissolved or dissolved or dispersed in a solvent.

A method of producing the composition of the present invention is hereinafter described in detail.

I. Preparation of Drug-Containing Core

The drug-containing core of the present invention (hereinafter sometimes abbreviate as core) to be coated with a coating composition can be prepared in any form. For example, uncoated tablets, pills, granules and fine granules are acceptable.

When the core is in a granule or fine granule form, its average particle diameter is preferably about 150 to about 2,000 $\mu$m, more preferably about 500 to about 800 $\mu$m. In this specification, granules having an average particle diameter about 500 $\mu$m or less is referred as "fine granule".

The core can be prepared by an ordinary production method. For example, it can be prepared by mixing the drug with an appropriate excipient, binder, disintegrant, lubricant etc., then conducting wet extrusion granulation, fluidized bed granulation, or the like.

The drug content of the core is about 0.5 to about 95% (w/w), preferably about 5.0 to about 60% (w/w), and more preferably about 30 to about 60% (w/w).

The excipient contained in the core is exemplified by saccharides, such as sucrose, lactose, mannitol and glucose, starch, crystalline cellulose and calcium phosphate.

Useful binders include polyvinyl alcohol, hydroxypropyl cellulose, macrogol, Pluronic F-68, gum arabic, gelatin and starch. Useful disintegrants include carboxymethyl cellulose calcium (ECG505), closslinked carboxymethylcellulose sodium (Ac—Di—Sol), polyvinylpyrrolidone and low-substitutional hydroxypropyl cellulose (L-HPC). Useful lubricants and antiflocculants include talc and magnesium stearate.

In addition to the above-described production method, the core can also be prepared by, for example, tumbling granulation, pan coating, fluidized bed coating and melting granulation in which the drug, or its mixture with a excipient, lubricant etc., is added little by little, while a binder, dissolved in an appropriate solvent, such as water or a lower alcohol (e.g., methanol, ethanol), is sprayed over an inert carrier particles for the core center. Useful inert carrier particles include those produced from sucrose, lactose, starch, crystalline cellulose or wax, their mean particle diameter being preferably about 100 $\mu$m to about 1,500 $\mu$m.

The core components are not limited to the above-mentioned substances, as long as they are pharmaceutically acceptable.

The surface of the resulting core may be coated with a protecting agent in order to separate the drug from the coating composition. The protecting agents include the above-mentioned hydrophilic substances. As protecting agents, polysaccharides having a hydroxyalkyl group or carboxyalkyl group are preferably used, with greater preference given to hydroxypropylmethyl cellulose. When a protecting agent is used, its coating ratio is about 1 to about 15% (w/w) to the core, preferably about 1 to about 10% (w/w), more preferably about 2 to about 8% (w/w).

The protecting agent can be coated by an ordinary coating method. Specifically, it can be coated by spray coating the core using, for example, fluidized bed coating or pan coating.

II. Coating the Core with Coating Composition

The composition of the present invention is produced by coating the core obtained in item I above with a liquid coating composition comprising one of the above-mentioned water-insoluble substance, swellable polymer and optionally hydrophilic substance either thermally dissolved or dissolved or dispersed in a solvent.

Useful methods for coating with a coating solution include the method in which the core obtained in item I above includes spray coating the core with the coating solution.

The content ratio of water-insoluble substance, swellable polymer and hydrophilic substance in the coating solution is chosen as appropriate range to make the content of each in the film fall in the above-mentioned range respectively.

The amount of coating composition used is about 1 to about 90% (w/w) to the core, preferably about 5 to about 50% (w/w), and more preferably about 10 to about 40% (w/w).

The solvent for the coating solution may be a water, an organic solvent or a mixture thereof. The mixing ratio of water and organic solvent (water/organic solvent, ratio by volume) may be varied between 1 and 100%, preferably 1 to about 30%. The organic solvent is not subject to limitation, as long as it is capable of dissolving the water-insoluble substance as mentioned about. Useful organic solvents include lower alcohols such as methyl alcohol, ethyl alcohol, isopropyl alcohol and n-butyl alcohol; lower alkanones such as acetone; acetonitrile; chloroform; and methylene chloride. Of these organic solvents, lower alcohols are preferred, with greater preference given to ethyl alcohol and isopropyl alcohol.

Water and its mixture with an organic solvent are preferably used as solvent of coating composition.

The spray coating procedure can be conducted by an ordinary coating method. Specifically, it can be conducted by spray coating the core by, for example, fluidized bed coating or pan coating. In this case, there may be added an appropriate antiflocculants such as talc, titanium dioxide etc., plasticizers such as glycerol fatty acid esters, hardened castor oil, triethyl citrate etc. and like.

The thus-obtained composition of the present invention may be administered as such, in the form of non-oral preparations (e.g., intramuscular, subcutaneous or visceral implant preparations, nasal, rectal or uterine transmucosal preparations) or oral preparations (e.g., granules, fine granules, tablets). When the composition is in a granule or fine granule form, it can be used as an oral preparation as packed in capsules etc.

The composition of the present invention is preferably used as an oral preparation.

With low toxicity, the composition of the present invention can be safely used in mammals in need (e.g., humans, bovines, swine, dogs, cats, mice, rats, rabbits) to treat or prevent their disease.

The dose of the composition of the present invention can be chosen as appropriate, as long as it ensures an effective amount of the drug, depending on the type and content of the drug, dosage form of the preparation, duration of drug release, target disease (the drug contained in the controlled-release composition of the present invention can be used against diseases which the drug has traditionally been used for), subject animal species etc. Generally, in cases where the drug is morphine hydrochloride, taking a once daily oral treatment or prevention of pain-associating condition as an example, the drug dose per administration can be chosen as appropriate over the range from about 4 mg to about 600 mg/day per cancer patient in need for treating pain-associating condition. However, the dose may be excess the above mentioned range, as long as it is administered safely, based on the condition of the patient.

In cases where the drug is morphine hydrochloride, the amount of the controlled-release composition of the present invention administered per administration can be chosen as appropriate over the range from about 10 mg to about 2,000 mg/day per cancer patient for treating pain-associating condition.

Because the controlled-release composition of the present invention contains a swellable polymer in its coating composition, the release rate of the active ingredient is increased over time during drug passage through the upper to lower small intestine and large intestine as the swellable polymer swells increasingly after administration, though the release of same is very limited in the stomach just after administration. The controlled-release composition of the present invention is therefore advantageous in that reduction in drug release from the controlled-release composition due to water loss is compensated to ensure sustained drug release for a long period of time exceeding 6 hours, more specifically 12 to 24 hours invivo, and maintain a constant drug concentration in plasma. Thus, the controlled-release composition of the invention can be advantageously used for once-daily oral administration. Specifically once-daily oral dosage form of opioid-analgesic such as morphien which produce a high biological availability is provided in the present invention. Especially the composition containing the polymers having an acidic dissociating group is preferable for this perpose in view of the pH-dependent swellability of the polymers.

The controlled-release composition of the present invention is also expected to have its transfer in the gastrointestinal tract delayed by the high viscosity of the swellable polymer in the coating composition, and also permit designing a sustained-release preparation capable of maintaining a fair drug concentration in plasma for a long period of time starting just after administration by the addition of a rapid-release preparation thereto.

EXAMPLES

The present invention is hereinafter described in more detail by means of, but is not limited to, the following working examples and experimental example.

Example 1

110 g of morphine hydrochloride, 480 g of lactose, 300 g of corn starch, 150 g of microcrystalline cellulose (Avicel), 30 g of carboxymethyl cellulose calcium (ECG-505) and 30 g of hydroxypropyl cellulose were mixed and added an appropriate amount of an aqueous solution of Pluronic F-68 (7% (w/w)), followed by kneading in a vertical granulator (FM-VG Fuji Sangyo). The resulting mixture was extruded using DOME GRAN (DG-L1, Fuji Paudal) and granulated using Marumerizer (OJ-230, Fuji Paudal). The resulting granular product was dried under reduced pressured (40° C., 15 hours), after which it was sieved and classified by size to yield 500 to 1,250 µm core granules. These core granules were placed in a spiral flow type coating machine (SFC-Labo, Freund Industrial Co. Ltd.) and spray coated with hydroxypropylmethyl cellulose dissolved in a mixture of ethanol and water (4:1 by volume) to yield coated core granules. The amount of hydroxypropylmethyl cellulose used was 3% (w/w) to the core granules. The resulting coated granules were then spray coated with a coating solution comprising ethyl cellulose, hydroxypropylmethyl cellulose and a crosslinked polyacrylic polymer (HIVISWAKO 104, Wako Pure Chemical) (70:10:20 by weight) to yield the desired composition. The coating procedure was conducted using a spiral flow type coating machine (SFC-Labo, Freund Industrial Co. Ltd.), the coating amount being 20% by weight to the core granules excluding the amount of hydroxypropylmethyl cellulose coating. Also, the coating solution was prepared by adding ethyl cellulose, hydroxypropylmethyl cellulose and the crosslinked acrylic polymer in the above-mentioned ratio to a mixture of ethanol and water (7:1 by volume), uniformly dispersing them in the mixture, and adding an appropriate amount of plasticizer.

Example 2

750 g of phenylpropanolamine hydrochloride, 103 g of corn starch, 162 g of microcrystalline cellulose (Avicel), 32.4 g of low-substituted hydroxypropyl cellulose and 32.4 g of hydroxypropyl cellulose were mixed and added an appropriate amount of water, followed by kneading in a vertical granulator (FM-VG, Fuji Sangyo). The resulting mixture was extruded using DOME GRAN (DG-L1, Fuji Paudal) and granulated using Marumerizer (OJ-230, Fuji Paudal). The resulting granular product was dried under reduced pressure (40° C., 15 hours), after which it was sieved and =classified by size to yield 500 to 1,250 µm core granules. These core granules were placed in a spiral flow type coating machine (SFC-Labo, Freund Industrial Co. Ltd.) and spray coated with hydroxypropylmethyl cellulose dissolved in a mixture of ethanol and water (4:1 by volume) to yield coated core granules. The amount of hydroxypropylmethyl cellulose used was 10% (w/w) to the core granules. The resulting coated granules were then spray coated with a coating solution comprising ethyl cellulose, hydroxypropylmethyl cellulose and a crosslinked acrylic polymer (Carbomer 934P) (80:5:15 by weight) to yield the desired composition. The coating procedure was conducted using a spiral flow type coating machine (SFC-Labo, Freund Industrial Co. Ltd.), the coating amount being 20% (w/w) to the core granules excluding the amount of hydroxypropylmethyl cellulose coating. Also, the coating solution was prepared by adding ethyl cellulose, hydroxypropylmethyl cellulose and the crosslinked acrylic polymer in the above-mentioned ratio to a mixture of ethanol and water (6:1 by volume), adding an appropriate amount of plasticizer, and stirring until a uniform mixture was obtained.

Example 3

750 g of phenylpropanolamine hydrochloride, 103 g of corn starch, 162 g of microcrystalline cellulose (Avicel), 32.4 g of low-substituted hydroxypropyl cellulose, and 32.4 g of hydroxypropyl cellulose were mixed and added an appropriate amount of water, followed by kneading in a vertical granulator (FM-VG Fuji Sangyo). The resulting mixture was extruded using DOME GRAN (DG-L1, Fuji Paudal) and granulated using Marumerizer (OJ-230, Fuji Paudal). The resulting granular product was dried under reduced pressure (40° C., 15 hours), after which it was sieved and classified by size to yield 500 to 1,250 µm core granules. These core granules were placed in a spiral flow type coating machine (SFC-Labo, Freund Industrial Co. Ltd.) and spray coated with hydroxypropylmethyl cellulose dissolved in a mixture of ethanol and water (4:1 by volume) to yield coated granules. The amount of hydroxypropylmethyl cellulose used was 3% (w/w) to the core granules. The resulting coated granules were then spray coated with a coating solution comprising ethyl cellulose, hydroxypropylmethyl cellulose and a crosslinked acrylic polymer (HIVISWAKO 104, Wako Pure Chemical) (70:15:15 by weight) to yield the desired composition. The coating procedure was conducted using a spiral flow type coating machine (SFC-Labo, Freund Industrial Co. Ltd.), the coating amount being 20% (w/w) to the core granules excluding the amount of hydroxypropylmethyl cellulose coating. Also, the coating solution was prepared by adding ethyl cellulose, hydroxypropylmethyl cellulose and the crosslinked acrylic polymer in the above-mentioned ratio to a mixture of ethanol and water (8:1 by volume), adding appropriate amounts of plasticizer and talc, and vigorously stirring until a uniform dispersion was obtained.

Example 4

To tetraglycerol pentabehenate, previously thermally molten at 80° C., morphine hydrochloride was added to a content of 10% (w/w). After vigorous stirring, the mixture was subjected to spray chilling to yield spherical particles, which were then sieved and classified by size to yield 177 to 500 µm fine granules. These fine granules were spray coated with a coating solution comprising ethyl cellulose dissolved in ethanol and a uniformly dispersed crosslinked acrylic polymer (HIVISWAKO 104, Wako Pure Chemical) (70:30 by weight) to yield the desired composition. The coating procedure was conducted using a spiral flow type coating machine (SFC-Labo, Freund Industrial Co. Ltd.), the coating amount being 20% (w/w) to the core granules.

Example 5

7.7 g of phenylpropanolamine hydrochloride, 42 g of lactose, 30 g of microcrystalline cellulose (Avicel), 30 g of closslinked carboxymethylcellulose sodium (AC—Di—Sol) and 0.3 g of magnesium stearate were mixed, followed by direct tableting to yield tablets (diameter of 6 mm). The resulting tablets were spray coated with a coating solution comprising ethyl cellulose, hydroxypropylmethyl cellulose and a crosslinked acrylic polymer (HIVISWAKO 104, Wako Pure Chemical) (70:15:15 by weight) to yield the desired composition. The coating procedure was conducted using a spiral flow type coating machine (SFC-Labo, Freund Industrial Co. Ltd.), the coating amount being 20% by weight to the core granules. Also, the coating solution was prepared by adding ethyl cellulose, hydroxypropylmethyl cellulose and the crosslinked acrylic polymer in the above-mentioned ratio to a mixture of ethanol and water (8:1 by volume), adding an appropriate amount of plasticizer, and uniformly dispersing the mixture.

Example 6

100 g of morphine hydrochloride, 42 g of corn starch, 40 g of microcrystalline cellulose (Avicel), 36 g of carboxymethyl cellulose calcium (ECG-505) and 36 g of hydroxypropyl cellulose were mixed and added an appropriate amount of an aqueous solution of polyoxyethylene (160) polyoxypropylen (30) glycol (Pluronic F-68) (6% (w/v)), followed by kneading in a mixing bowl. The resulting mixture was extruded using DOME GRAN (DG-L1, Fuji Paudal) and granulated using Marumerizer (OJ-230, Fuji Paudal). After being dried under reduced pressured (40° C., 16 hours), the resulting granular product it was sieved and classified by size to yield 500 to 1,250 µm granules. These core granules were placed in a spiral flow type coating machine (SFC-Labo, Freund Industrial Co. Ltd.) and spray coated with hydroxypropylmethyl cellulose dissolved in a mixture of ethanol and water (4:1 by volume) to yield coated core granules. The amount of hydroxypropylmethyl cellulose used was 3% (w/w) to the core granules. The resulting coated granules were coated with a coating solution comprising ethyl cellulose, hydroxypropylmethyl cellulose and a crosslinked polyacrylic polymer (HIVISWAKO 104; Wako Pure Chemical) (70:20:10 by weight) to yield the desired composition. The coating procedure was conducted using a spiral flow type coating machine (SFC-Labo, Freund Industrial Co. Ltd.), the coating amount being 20% by weight to the core granules excluding the amount of hydroxypropylmethyl cellulose coating. Also, the coating solution was prepared by adding ethyl cellulose, hydroxypropylmethyl cellulose and the crosslinked acrylic polymer in the above-mentioned ratio to a mixture of ethanol and water (7:1 by volume), uniformly dispersing them in the mixture, and adding an appropriate amount of plasticizer.

Example 7

100 g of morphine hydrochloride, 42 g of corn starch, 40 g of microcrystalline cellulose (Avicel), 36 g of carboxymethyl cellulose calcium (ECG-505) and 36 g of hydroxypropyl cellulose were mixed and added an appropriate amount of an aqueous solution of polyoxyethylene (160) polyoxypropylen (30) glycol (Pluronic F-68) (6% (w/v)), followed by kneading in a mixing bowl. The resulting mixture was extruded using DOME GRAN (DG-L1, Fuji Paudal) and granulated using Marumerizer (OJ-230, Fuji Paudal). After being dried under reduced pressured (40° C., 16 hours), the resulting granular product it was sieved and classified by size to yield 500 to 1,250 µm granules. These core granules were placed in a spiral flow type coating machine (SFC-Labo, Freund Industrial Co. Ltd.) and spray coated with hydroxypropylmethyl cellulose dissolved in a mixture of ethanol and water (4:1 by volume) to yield coated core granules. The amount of hydroxypropylmethyl cellulose used was 3% (w/w) to the core granules. The resulting coated granules were coated with a coating solution comprising ethyl cellulose, hydroxypropylmethyl cellulose and a crosslinked polyacrylic polymer (HIVISWAKO 104; Wako Pure Chemical) (70:20:10 by weight) to yield the desired composition. The coating procedure was conducted using a spiral flow type coating machine (SFC-Labo, Freund Industrial Co. Ltd.), the coating amount being 30% by weight to the core granules excluding the amount of hydroxypropylmethyl cellulose coating. Also, the coating solution was prepared by adding ethyl cellulose, hydroxypropylmethyl cellulose and the crosslinked acrylic polymer in the above-mentioned ratio to a mixture of ethanol and water (7;1 by volume), uniformly dispersing them in the mixture, and adding an appropriate amount of plasticizer.

Example 8

100 g of morphine hydrochloride, 42 g of corn starch, 40 g of microcrystalline cellulose (Avicel), 36 g of carboxymethyl cellulose calcium (ECG-505) and 36 g of hydroxypropyl cellulose were mixed and added an appropriate amount of an aqueous solution of polyoxyethylene (160) polyoxypropylen (30) glycol (Pluronic F-68) (6% (w/v)), followed by kneading in a mixing bowl. The resulting mixture was extruded using DOME GRAN (DG-L1, Fuji Paudal) and granulated using Marumerizer (OJ-230, Fuji Paudal). After being dried under reduced pressure (40° C., 16 hours), the resulting granular product was sieved and classified by size to yield 500 to 1,250 μm granules. These core granules were placed in a spiral flow type coating machine (SFC-Labo, Freund Industrial Co. Ltd.) and spray coated with hydroxypropylmethyl cellulose dissolved in a mixture of ethanol and water (4:1 by volume) to yield coated core granules. The amount of hydroxypropylmethyl cellulose used was 3% (w/w) to the core granules. The resulting coated granules were coated with a coating solution comprising ethyl cellulose, hydroxypropylmethyl cellulose and a crosslinked polyacrylic polymer (HIVISWAKO 104; Wako Pure Chemical) (60:25:15 by weight) to yield the desired composition. The coating procedure was conducted using a spiral flow type coating machine (Freund Industrial Co. Ltd., SFC-Labo), the coating amount being 30% by weight to the core granules excluding the amount of hydroxypropylmethyl cellulose coating. Also, the coating solution was prepared by adding ethyl cellulose, hydroxypropylmethyl cellulose and the crosslinked acrylic polymer in the above-mentioned ratio to a mixture of ethanol and water (7:1 by volume), uniformly dispersing them in the mixture, and adding an appropriate amount of plasticizer.

Example 9

150 g of morphine hydrochloride, 63 g of corn starch, 60 g of microcrystalline cellulose (Avicel), 9 g of carboxymethyl cellulose calcium (ECG-505) and 9 g of hydroxypropyl cellulose were mixed and added an appropriate amount of an aqueous solution of Pluronic F-68 (6% (w/w)), followed by kneading in a mortar. The mixture was then extruded using DOME GRAN (DG-L1, Fuji Paudal) and granulated using Marumerizer (OJ-230, Fuji Paudal). After being dried under reduced pressured (40*C, 15 hours), the resulting granular product was sieved and classified by size to yield 500 to 1,250 μm core granules. These core granules were placed in a spiral flow type coating machine (SFC-Labo, Freund Industrial Co. Ltd.) and spray coated with hydroxypropylmethyl cellulose dissolved in a mixture of ethanol and water (4:1 by volume) to yield coated granules. The amount of hydroxypropylmethyl cellulose used was 3% (w/w) relative to the core granules. The coated granules obtained were then spray coated with a coating liquid comprising ethyl cellulose, hydroxypropylmethyl cellulose and a crosslinked polyacrylic acid polymer (HIVISWAKO 104, Wako Pure Chemical Industries) (70:10:20 by weight) to yield the desired composition. The coating procedure was conducted using a spiral flow type coating machine (SFC-Labo, Freund Industrial Co. Ltd.), the coating amount being 10% by weight relative to the core granules excluding the amount of hydroxypropylmethyl cellulose coating. The dispersion was prepared by adding ethyl cellulose, hydroxypropylmethyl cellulose and a crosslinked acrylic acid polymer in the above-mentioned ratio to a mixture of ethanol and water (6:1 by volume), uniformly dispersing them in the mixture, and adding an appropriate amount of plasticizer.

Example 10

150 g of morphine hydrochloride, 63 g of corn starch, 60 g of microcrystalline cellulose (Avicel), 9 g of carboxymethyl cellulose calcium (ECG-505) and 9 g of hydroxypropyl cellulose were mixed and added an appropriate amount of an aqueous solution of Pluronic F-68 (6% (w/w)), followed by kneading in a mortar. The mixture was then extruded using DOME GRAN (DG-L1, Fuji Paudal) and granulated using Marumerizer (OJ-230, Fuji Paudal). After being dried under reduced pressured (40° C., 15 hours), the resulting granular product was sieved and classified by size to yield 500 to 1,250 μm core granules. The resulting core granules were placed in a spiral flow type coating machine (SFC-Labo, Freund Industrial Co. Ltd.) and sprayed with an aqueous solution of hydroxypropylmethyl cellulose to yield coated core granules. The amount of hydroxypropylmethyl cellulose used was 5% (w/w) relative to the core granules. The coated core granules obtained were then coated with a coating film comprising a polymer mixture (weight ratio: ethyl cellulose:crosslinked acrylic acid polymer=80:20) by spraying with an aqueous dispersion containing ethyl cellulose and a crosslinked acrylic acid polymer (Carbomer 934P, BF Goodrich) to yield the desired composition. The coating procedure was conducted using a spiral flow type coating machine (SFC-Labo, Freund Industrial Co. Ltd.), the coating amount being 35% (w/w) relative to the core granules excluding the amount of hydroxypropylmethyl cellulose coating. The coating liquid was prepared by adding an appropriate amount of acetylated monoglyceride (Myvacet 9–40, Koyo Shokai) as a plasticizer, and a crosslinked acrylic acid polymer in the above-mentioned ratio to a commercially available aqueous suspension of ethyl cellulose (Aquacoat, Asahi Chemical Industry), and diluting the mixture with an appropriate amount of water to yield a uniform dispersion.

Example 11

150 g of morphine hydrochloride, 63 g of corn starch, 60 g of microcrystalline cellulose (Avicel), 9 g of carboxymethyl cellulose calcium (ECG-505) and 9 g of hydroxypropyl cellulose were mixed and added an appropriate amount of an aqueous solution of Pluronic F-68 (6% (w/w)), followed by kneading in a mortar. The mixture was then extruded using DOME GRAN (DG-L1, Fuji Paudal) and granulated using Marumerizer (OJ-230, Fuji Paudal). After being dried under reduced pressured (40° C., 15 hours), the resulting granular product was sieved and classified by size to yield 500 to 1,250 μm core granules. The core granules obtained were placed in a spiral flow type coating machine (SFC-Labo, Freund Industrial Co. Ltd.) and coated with 7% (w/w) ethyl cellulose relative to the core granules as an intermediate layer. The coating liquid was prepared by adding an appropriate amount of triethyl citrate (Citroflex, Pfizer Pharmaceuticals) to a commercially available aqueous suspension of ethyl cellulose (Aquacoat, Asahi Chemical Industry), and diluting the mixture with an appropriate amount of water. The coated core granules obtained were then coated with a coating film comprising ethyl cellulose, hydroxypropylmethyl cellulose and a crosslinked acrylic acid polymer (HIVISWAKO 104, Wako Pure Chemical Industries) (70:10:20 by weight) by amount of 35% (w/w) relative to the core granules excluding the amount of hydroxypropylmethyl cellulose coating using a spiral flow type coating machine (SFC-Labo, Freund Industrial Co. Ltd.), and dried (80° C., 2 hr) to yield the desired composition. The coating liquid was prepared by adding an appropriate amount of triethyl citrate (Citroflex, Pfizer Pharmaceuticals) as a plasticizer to an aqueous suspension of ethyl cellulose (Aquacoat, Asahi Chemical Industry), further adding hydroxypropylmethyl cellulose and a crosslinked acrylic acid polymer in the above-mentioned ratio, and stirring the mixture to yield a uniform liquid.

Experimental Example 1

The composition obtained in Example 1 was subjected to an in vitro dissolution test.

The test was subjected by Method I (acidic conditions) and Method II (neutral conditions) described in the Japanese Pharmacopoeia XII as follows:

Method I : Dissolution Test I (paddle method) [first solution (pH 1.2), 900 ml, 37° C., 100 rpm]

Method II: Dissolution Test I (paddle method) [50 mM citrate buffer (pH 6.8), 900 ml, 37° C., 100 rpm]

Figure 1:
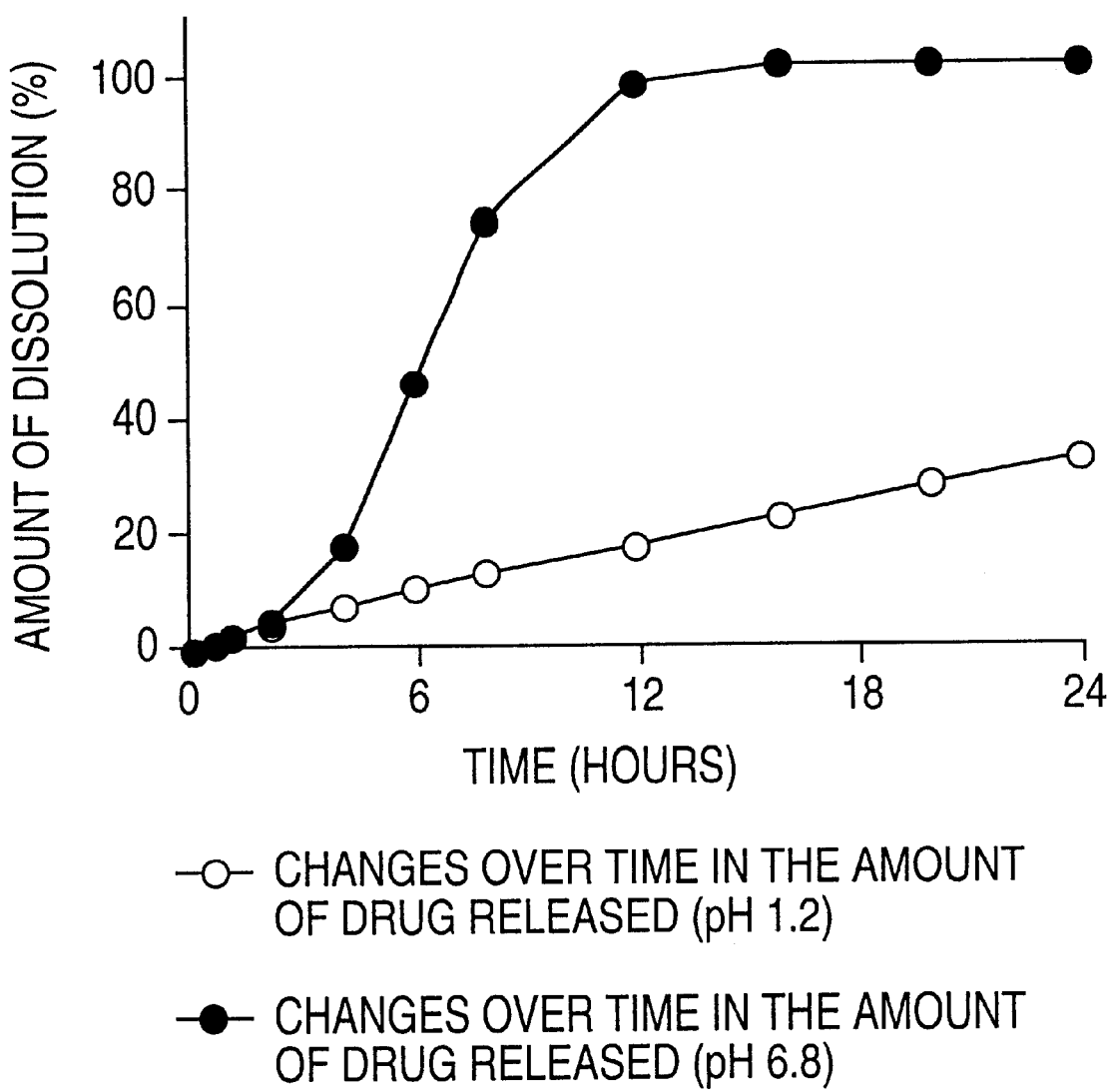
FIGS. 1 and 2 show the effect of pH on the amount of drug (morphine hydrochloride) released invitro.

The test results are shown in FIG. 1.

As seen from FIG. 1, the amount of drug (morphine hydrochloride) dissolved was suppressed at pH 1.2, corresponding to intragastric pH (—○—), with a dissolution rate of about 40% even at 24 hours after test initiation. On the other hand, at pH 6.8, rapid dissolution occurred a(—●—), with a 6-hour dissolution rate almost equivalent to the 24-hour dissolution rate at pH 1.2, and a 12-hour dissolution rate of about 100%.

Experimental Example 2

The composition obtained in Example 9 was subjected to an in vitro dissolution test and assessed as to in vivo absorption in beagle dogs.

The dissolution test was conducted as described in Experimental Example 1 in accordance with Test Methods I (acidic conditions) and II (neutral conditions).

Figure 2:
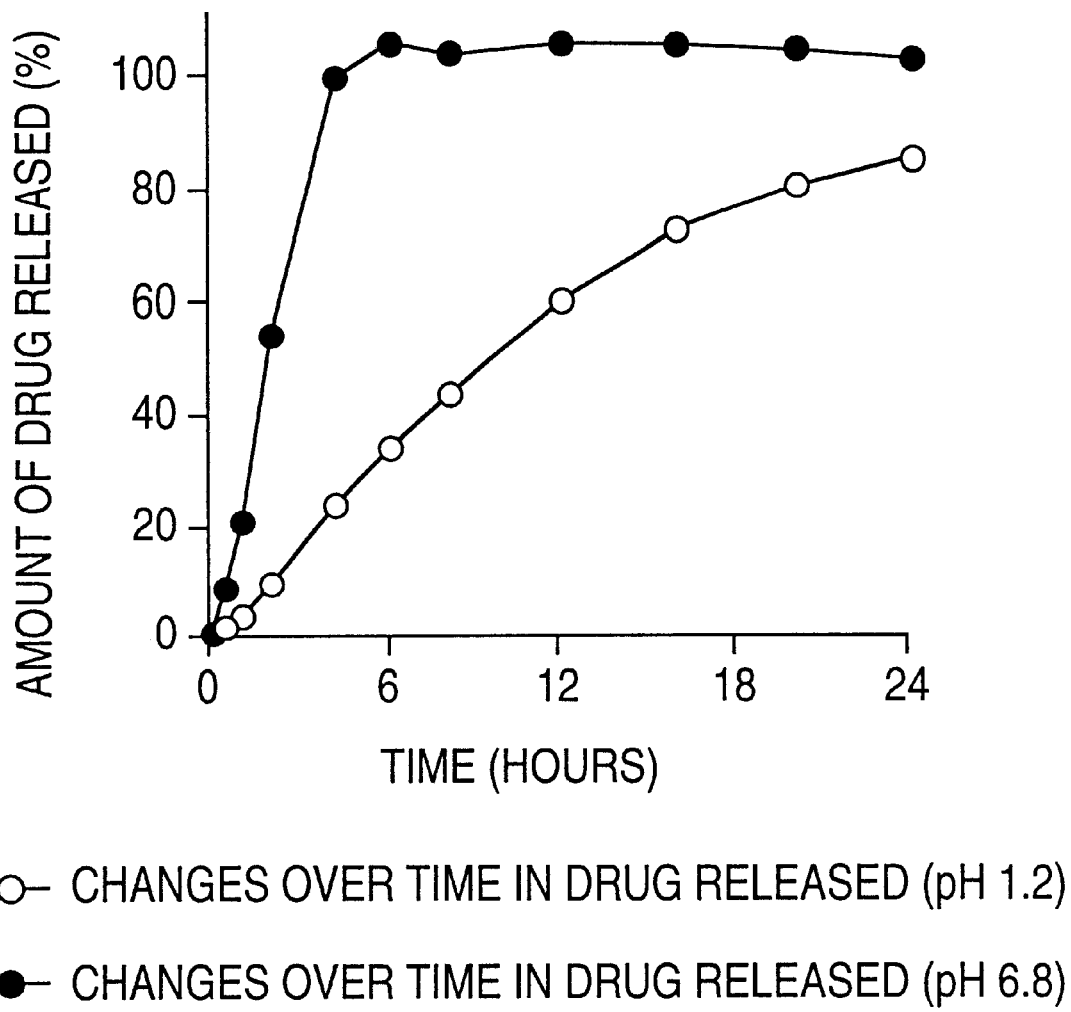

The results of the dissolution test are shown in FIG. 2.

As is evident from FIG. 2, the dissolution amount of drug (morphine hydrochloride) at pH 1.2, equivalent to intragastric pH (—○—), was smaller than that at pH 6.8 (—●—). At 6 hours after test initiation, percent dissolution rates (drug release rates) were about 35% at pH 1.2 and about 100% at pH 6.8.

Experimental Example 3

The composition obtained in Example 9 was administered to beagle dogs; changes over time in the drug's plasma concentration were compared with those of the control MS Contin® (Purdue Frederick Company), a commercially available sustained-release morphine preparation. Specifically, the composition (containing 30 mg of morphine) or MS Contin® was administered to five fasted beagle dogs; at 1, 2, 4, 6, 8, 10, 12, 15, 18 and 24 hours after administration, blood samples were taken and assayed for plasma concentration of morphine. After a 1-week washout, the same experiment was conducted.

The results are shown in FIG. 3.

The $T_{max}$ (time to maximum plasma drug concentration) in MS Contin® administration was 2 hours; the plasma drug concentration-declined gradually thereafter. On the other hand, the $T_{max}$ in administration of the composition obtained in Example 9 was 6 hours; the plasma drug concentration was remained at high levels exceeding 10 ng/ml until 18 hours after administration. The 24-hour AUC (area under the curve) values were 276 ng·hr/ml for MS Contin® and 460 ng·hr/ml for the composition obtained in Example 9, demonstrating that the composition of the present invention makes it possible to retain sufficient plasma drug concentrations without BA reduction.

The controlled-release composition of the present invention, especially in the form of oral preparations, is capable of maintaining a sufficient drug concentration in blood over an extended period of time by suppressing drug release in the stomach, through which it passes initially after administration, then accelerating drug release in the small and large intestines.

What is claimed is:

1. A controlled-release composition comprising a drug-containing core coated with a coating composition comprising (i) a water-insoluble ethyl cellulose (ii) a crosslinked acrylic polymer having an acidic dissociating group and which shows pH-dependent swelling.

2. A method of producing a controlled-release composition which comprises coating a drug-containing core with a coating composition comprising (i) a water-insoluble ethyl cellulose and (ii) crosslinked acrylic polymer having an acidic disassociating group and which shows a pH dependent swelling.

3. The method of claim 2, wherein said pH dependent swelling is having a small degree of swelling under acidic pH levels and swells at neutral pH levels.

4. The controlled release composition of claim 1, wherein said pH dependent swelling is having a small degree of swelling under acidic pH levels and swells at neutral pH levels.

5. The controlled-release composition of claim 1, wherein said drug is a sympathomimetics.

6. The controlled-release composition of claim 1, wherein the content of said drug is not lower than 0.5% (w/w).

7. The controlled-release composition of claim 1 in the form of granules, fine granules, tablets or capsules.

8. The controlled-release composition of claim 1, wherein the viscosity of said cross linked acrylic polymer is about 1,500 to about 60,000 cp in 0.2% neutral solution.

9. The controlled-release composition of claim 1, wherein said coating composition further comprises a (iii) hydrophilic substance.

10. The controlled-release composition of claim 9, wherein said hydrophilic substance is a polysaccharide having a hydroxyalkyl group or carboxyalkyl group.

11. The controlled-release composition of claim 9, wherein said hydrophilic substance is hydroxypropylmethyl cellulose.

12. The controlled-release composition of claim 1, wherein the ratio of weight of said coating composition to said core is not lower than 1:100.

13. The controlled-release composition of claim 1, wherein the content ratios of (i) the water-insoluble ethyl cellulose and (ii) crosslinked acrylic polymer in said coating composition are about 40 to about 95% (w/w) and about 1 to about 40% (w/w), respectively.

14. The controlled-release composition of claim 9, wherein the content ratios of (i) the water-insoluble ethyl cellulose (ii) crosslinked acrylic polymer and (iii) hydrophillic substance in said coating composition are about 40 to about 95% (w/w), about 1 to about 40% (w/w), and about 0 to about 40% (w/w), respectively.

15. The controlled-release composition of claim 1, wherein said drug is an opioid compound.

16. The controlled-release composition of claim 14, wherein said drug is morphine or a salt thereof.

17. A method for the treatment of pain-associated condition which comprises administering to a mammal in need thereof an effective amount of medicament containing the controlled-release composition of claim 16.

18. A method for the treatment of pain-associated condition which comprises administering to a mammal in need thereof an effective amount of medicament containing the controlled-release composition of claim 5.

19. The controlled-release composition of claim 9, wherein said hydrophilic substance is hydroxypropyl cellulose.

20. The controlled-release composition of claim 9, wherein said hydrophilic substance is polyethylene glycol.

21. The controlled-release composition of claim 1, which is produced by preparing a drug-containing core, and coating the resulting core by spray coating with a liquid coating composition comprising a water-soluble ethyl cellulose and a crosslinked acrylic polymer having an acidic dissociating group and which shows pH-dependent swelling either thermally dissolved or dispersed in a solvent.

22. The method of claim 2, wherein coating is conducted by spray coating.

* * * * *